(12) United States Patent
Veasey et al.

(10) Patent No.: US 7,094,221 B2
(45) Date of Patent: Aug. 22, 2006

(54) DRIVE MECHANISMS SUITABLE FOR USE IN DRUG DELIVERY DEVICES

(75) Inventors: Robert Frederick Veasey, Leamington Spa (GB); Robert Perkins, Leamington Spa (GB); David Aubrey Plumptre, Droitwich (GB)

(73) Assignee: DCA Design International Ltd., Warwick (GB)

( * ) Notice: Subject to any disclaimer, the term of this patent is extended or adjusted under 35 U.S.C. 154(b) by 96 days.

(21) Appl. No.: 10/790,026

(22) Filed: Mar. 2, 2004

(65) Prior Publication Data

US 2004/0260247 A1    Dec. 23, 2004

(30) Foreign Application Priority Data

Mar. 3, 2003    (GB)    ................................. 0304824.6

(51) Int. Cl.
*A61M 5/00*    (2006.01)
(52) U.S. Cl. ...................... 604/187; 604/207; 604/208
(58) Field of Classification Search ................ 604/187, 604/110, 68, 181, 207, 209, 211
See application file for complete search history.

(56) References Cited

U.S. PATENT DOCUMENTS

| 5,304,152 | A |  | 4/1994 | Sams |
| 5,674,204 | A |  | 10/1997 | Chanoch |
| 5,688,251 | A |  | 11/1997 | Chanoch |
| 5,800,388 | A | * | 9/1998 | Schiff et al. .................. 604/68 |
| 6,004,297 | A | * | 12/1999 | Steenfeldt-Jensen et al. .... 604/207 |
| 6,221,046 | B1 | * | 4/2001 | Burroughs et al. ......... 604/153 |
| 2002/0029018 | A1 | * | 3/2002 | Jeffrey ........................ 604/209 |
| 2004/0059299 | A1 |  | 3/2004 | Moller |

FOREIGN PATENT DOCUMENTS

| EP | 0 937 471 A2 | 8/1999 |
| WO | WO 91/14467 | 10/1991 |
| WO | WO 99/38554 | 8/1999 |

* cited by examiner

*Primary Examiner*—Nicholas D. Lucchesi
*Assistant Examiner*—Melissa A. McCorkle
(74) *Attorney, Agent, or Firm*—Finnegan, Henderson, Farabow, Garrett & Dunner

(57) ABSTRACT

A drive mechanism suitable for use in drug delivery devices is disclosed. The drive mechanism may be used with injector-type drug delivery devices, such as those permitting a user to set the delivery dose. The drive mechanism may include a housing, a dose dial sleeve having a helical thread of a first lead, and a two-part piston rod. The two-part piston rod may include an outer part having a helical thread of a second lead and an inner part having a helical thread of a third lead. In such an embodiment, the first lead of the thread of the dose dial sleeve may be equal to the sum of the second lead of the thread of the outer part of the piston rod and the third lead of the thread of the inner part of the piston rod.

18 Claims, 4 Drawing Sheets

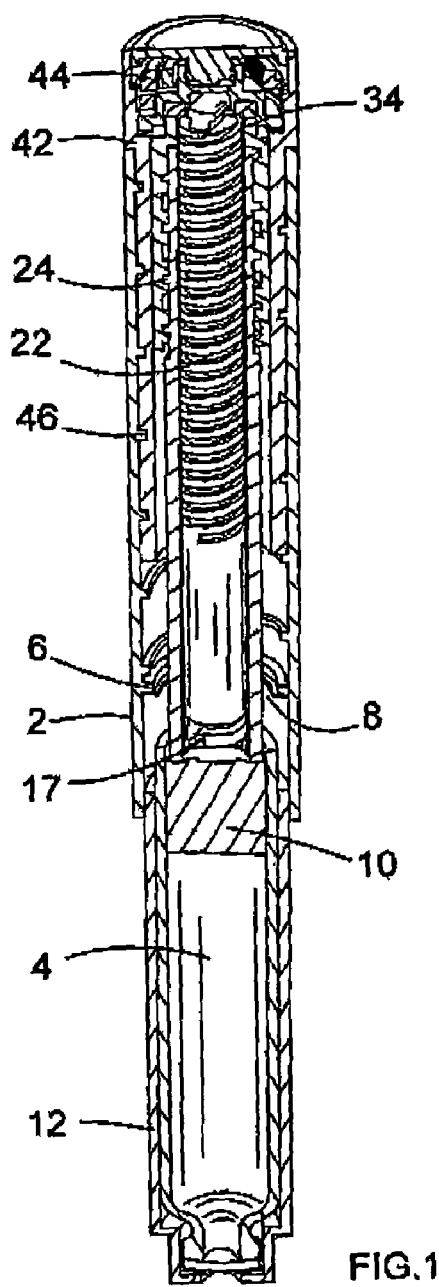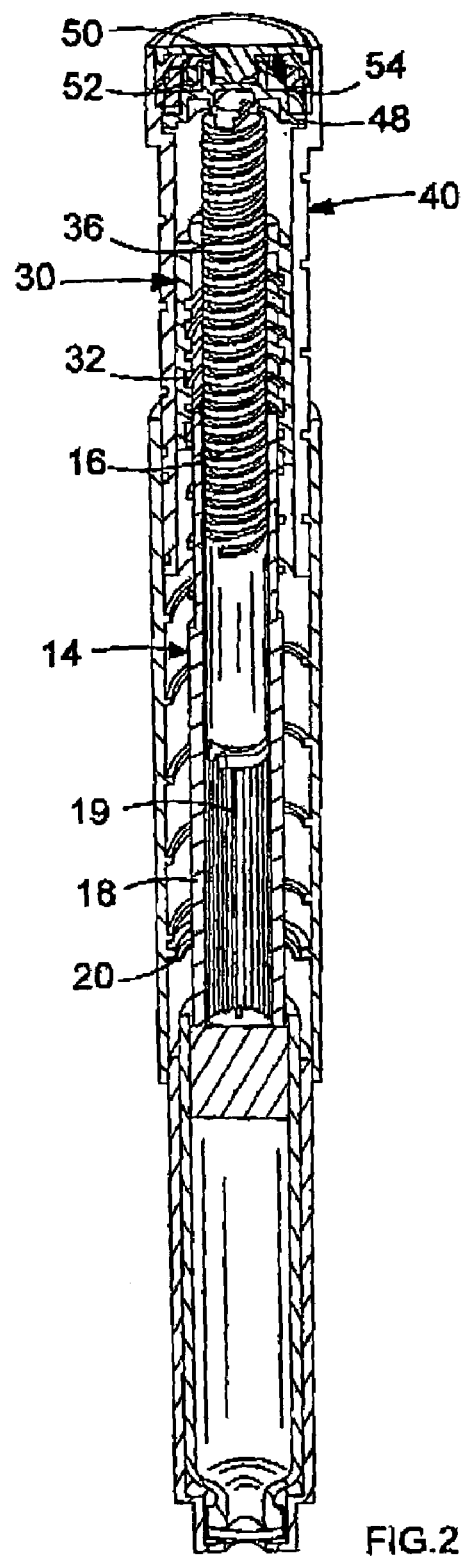

DRIVE MECHANISMS SUITABLE FOR USE IN DRUG DELIVERY DEVICES

THE TECHNICAL FIELD OF THE INVENTION

The present invention relates to drive mechanisms suitable for use in drug delivery devices, in particular pen-type injectors, having dosage setting means, enabling the administration of medicinal products from a multidose cartridge. In particular, the present invention relates to such drug delivery devices where a user may set the dose.

DESCRIPTION OF RELATED ART

Such drug delivery devices have application where regular injection by persons without formal medical training occurs, i.e., patients. This is increasingly common amongst those having diabetes where self-treatment enables such persons to conduct effective management of their diabetes.

These circumstances set a number of requirements for drug delivery devices of this kind. The device must be robust in construction, yet easy to use in terms of the manipulation of the parts, understanding by a user of its operation and the delivery of the required dose of medicament. Dose setting must be easy and unambiguous. In the case of those with diabetes, many users will be physically infirm and may also have impaired vision requiring the drive mechanism to have low dispensing force and an easy to read dose setting display. Where the device is to be disposable rather than reusable, the device should be cheap to manufacture and easy to dispose of (preferably being suitable for recycling). To meet these requirements the number of parts required to assemble the device and the number of material types the device is made from need to be kept to a minimum.

User operated drug delivery devices comprising a telescopic piston rod are well known within the medical field.

WO 9114467 A1 discloses a dispensing device, comprising a drive mechanism having a telescopic piston rod consisting of a first and a second threaded member having equi-spaced threaded segments with non-threaded segments therebetween. The device further comprises a dose setting sleeve, which surrounds the second threaded member being coupled for rotation and is threadedly engaged with the device shell. The threads of the three said components are of the same lead. The design of this device requires a body length to plunger length ratio of about 1:1 in order to allow dispensing of relatively large doses. However, simple and safe correction of a set overdose remains unresolved without either dispensing the set amount of fluid or dismantling the cartridge.

Surprisingly it was found that the drive mechanism according to instant invention provides a valuable technical alternative for the design of a compact drive mechanism, which requires relatively low force to actuate the mechanism, further providing the advantage of safe dose dialling and dispensing. Furthermore, the drive mechanism according to instant invention provides the advantage of intuitive and easy to use correction of a set dose.

DESCRIPTION OF THE INVENTION

According to a first aspect of the present invention, a drive mechanism for use in a drug delivery device is provided, comprising
a housing;
a dose dial sleeve having a helical thread of a first lead; and
a two-part piston rod; characterised in that
the said piston rod comprising an outer part having an external helical thread of a second lead and an inner part having an external helical thread of a third lead, whereby the first lead of the thread of the dose dial sleeve is equal to the sum of the second lead of the thread of the outer part of the piston rod and the third lead of the thread of the inner part of the piston rod.

The term "drug delivery device" according to instant invention shall mean a single-dose or multi-dose, disposable or re-useable device designed to dispense a selected dose of a medicinal product, preferably multiple selected doses, e.g. insulin, growth hormones, low molecular weight heparins, and their analogues and/or derivatives etc. Said device may be of any shape, e.g. compact or pen-type. Dose delivery may be provided through a mechanical (optionally manual) or electrical drive mechanism or stored energy drive mechanism, such as a spring, etc. Dose selection may be provided through a manual mechanism or electronic mechanism. Additionally, said device may contain components designed to monitor physiological properties such as blood glucose levels, etc. Furthermore, the said device may comprise a needle or may be needle-free. In particular, the term "drug delivery device" shall mean a disposable multi-dose pen-type device having mechanical and manual dose delivery and dose selection mechanisms, which is designed for regular use by persons without formal medical training such as patients. Preferably, the drug delivery device is of the injector-type.

The term "housing" according to instant invention shall preferably mean any exterior housing ("main housing", "body", "shell") or interior housing ("insert", "inner body"). The housing may be designed to enable the safe, correct, and comfortable handling of the drug delivery device or any of its mechanism. Usually, it is designed to house, fix, protect, guide, and/or engage with any of the inner components of the drug delivery device (e.g., the drive mechanism, cartridge, plunger, piston rod) by limiting the exposure to contaminants, such as liquid, dust, dirt etc. In general, the housing may be unitary or a multipart component of tubular or non-tubular shape. Usually, the exterior housing serves to house a cartridge from which a number of doses of a medicinal product may by dispensed.

In further embodiments of instant invention, the exterior housing, the dose dial sleeve and/or the drive sleeve are provided with one or more maximum dose stops adapted to be abutted by a corresponding radial stop provided on the respective corresponding engaging component.

The term "engaged" according to instant invention shall particularly mean the interlocking of two or more components of the drive mechanism/drug delivery device, e.g. a spline or thread connection, preferably the interlocking of helical threads of components ("threadedly engaged").

The term "helical thread" according to instant invention shall preferably mean a full or part thread, e.g., a cylindrical spiral rib/groove, located on the internal and/or external surface of a component of the drug delivery device, having an essentially triangular or square or rounded section designed to allow continuous free rotational and/or axial movement between components. Optionally, said thread may be further designed to prevent rotational or axial movement of certain components in one direction.

The term "dose dial sleeve" according to instant invention shall mean an essentially tubular component of essentially circular cross-section having either:
 a) both an internal and external thread, or
 b) an internal thread, or
 c) an external thread.

Preferably, the dose dial sleeve according to instant invention comprises a helical thread having a lead, which is similar to, preferably the same as the sum of the leads of the helical threads of the inner and the outer part of the two-part piston rod. In another preferred embodiment of instant invention, the dose dial sleeve is threadedly engaged with the housing, and, in a particular embodiment, the dose dial sleeve comprises a first section of a first diameter and a second section of a second diameter, whereby the outer surface of the first section of the dose dial sleeve is threadedly engaged with the housing.

In yet another preferred embodiment the dose dial sleeve is designed to indicate a selected dose of a dispensable product. This may be achieved by use of markings, symbols, numerals, etc., e.g. printed on the external surface of the dose dial sleeve or an odometer, or the like.

The term "lead" according to instant invention shall preferably mean the axial distance a nut would advance in one complete revolution; preferably "lead" shall mean the axial distance through which a component having a helical thread, i.e. dose dial sleeve, drive sleeve, piston rod, etc., of the drive mechanism travels during one rotation. Therefore lead is a function of the pitch of the thread of the relevant component.

The term "pitch" according to instant invention shall preferably mean the distance between consecutive contours on a helical thread, measured parallel to the axis of the helical thread.

Optionally, the drive mechanism of instant invention further comprises a drive sleeve, whereby the term "drive sleeve" according to instant invention shall mean any essentially tubular component of essentially circular cross-section and which is engaged with the dose dial sleeve, and is even more preferred further engaged with the piston rod.

In a particular embodiment of instant invention, the drive sleeve comprises a helical thread along an internal surface extending from a first end of the drive sleeve towards an internal land, the land being further provided with a radially inwardly directed flange.

The term "releasibly connected" according to instant invention shall preferably mean that two components of instant mechanism or device are reversibly joined to each other, which allows coupling and decoupling, e.g. by means of a clutch.

The term "piston rod" according to instant invention shall mean any two-part component adapted to operate through/within the housing, designed to translate axial movement through/within the drug delivery device, preferably from the drive sleeve to the piston, for the purpose of discharging/dispensing an injectable product. The "two-part piston rod" of instant invention shall further mean a component having a circular or non-circular cross-section. It may be made of any suitable material known by a person skilled in the art.

The term "two-part piston rod" according to instant invention comprises an outer and an inner component ("outer part" and "inner part") and at least two helical threads, preferably an external helical thread on the outer part and an external helical thread on the inner part, In other preferred embodiments of instant invention, the sum of the leads of the said threads of the inner and outer part of the "two-part piston rod" is equal to the lead of the thread of the dose dial sleeve. The meaning of the term "is equal to" according to instant invention shall encompass similar, essentially the same, or the same values of the leads of the said threads, whereby it is essentially provided that the function of the threaded engagement of the above mentioned threaded components is maintained. Optionally, the leads of the said threads of the inner and outer part of the said piston rod are of opposite dispositions. One of the said threads may be designed to engage with the drive sleeve. In still another preferred embodiment of instant invention the inner and the outer part of the said piston rod are adapted for longitudinal displacement but are restricted for rotation with respect to each another.

In another preferred embodiment of the invention, the outer part of the said piston rod is adapted for longitudinal displacement only with respect to the housing, e.g., by a ratchet means. In one particular embodiment of instant invention, the said ratchet means is in the form of barbs or tangs extending from the housing.

The term "first end" according to instant invention shall mean the proximal end. The proximal end of the device or a component of the device shall mean the end, which is closest to the dispensing end of the device.

The term "second end" according to instant invention shall mean the distal end. The distal end of the device or a component of the device shall mean the end, which is furthest away from the dispensing end of the device.

Optionally, the drive mechanism of instant invention further comprises a clutch means, whereby the term "clutch means" according to instant invention shall mean any clutch, which releasibly connects the dose dial sleeve and the inner part of the said piston rod and which is designed to allow rotation of the dose dial sleeve and the inner part of the said piston rod with respect to the housing when the dose dial sleeve and the inner part of the said piston rod are coupled. Particularly, the clutch means couples the inner part of the piston rod to the dose dial sleeve thereby preventing rotation between the inner part of the piston rod and the dose dial sleeve when engaged. Preferably, the clutch means is located between the dose dial sleeve and the said piston rod, in particular, the inner part of the said piston rod.

Accordingly, the term clutch means is any clutch engaging for the purpose of reversibly locking two components in rotation, e.g., by use of axial forces to engage a set of face teeth (saw teeth, dog teeth, crown teeth) or any other suitable frictional faces.

In one particular embodiment of instant invention, the clutch means comprises a plurality of radially extending longitudinally directed teeth provided respectively on the dose dial sleeve and a disc connected to the inner part of the piston rod.

In still another embodiment of instant invention, the drive mechanism comprises a clicker means, e.g., disposed between the clutch means and the dose dial sleeve, between the inner and the outer part of the piston rod, or wherever applicable.

Optionally, the clicker means comprising an inserted component having an upper part and a lower part depending therefrom, the upper part of the inserted component is provided on an internal surface with a plurality of circumferentially spaced longitudinally extending teeth, the lower part of the inserted component comprising a flexible toothed member being disposed in alignment with a plurality of circumferentially disposed longitudinally directed teeth provided on an inner surface of the dose dial sleeve, and the inner surface of the upper part of the inserted component having a plurality of circumferentially disposed longitudinally extending teeth being disposed in alignment with a flexible toothed member provided on the clutch means such that relative rotation between the dose dial sleeve and the clutch means causes one of the flexible toothed members to ride over corresponding longitudinally directed teeth to produce a series of clicks.

A second aspect of instant invention provides an assembly for use in a drug delivery device comprising the drive mechanism according to instant invention.

A third aspect of the present invention provides a drug delivery device comprising the drive mechanism or the assembly according to instant invention.

A fourth aspect of the present invention provides a method of assembling a drug delivery device comprising the step of providing a drive mechanism or an assembly according to instant invention.

A fifth aspect of instant invention is the use of a drug delivery device according to instant invention for dispensing a medicinal product preferably dispensing a pharmaceutical formulation (e.g. solution, suspension etc.) comprising an active compound selected from the group consisting of insulin, growth hormone, low molecular weight heparin, their analogues, and their derivatives.

BRIEF DESCRIPTION OF THE DRAWINGS

Without any limitation, the instant invention will be explained in greater detail below in connection with a preferred embodiment and with reference to the drawings in which:

FIG. 1 shows a sectional view of an embodiment of the drug delivery device according to the present invention in a first, cartridge full, position;

FIG. 2 shows a sectional view of the drug delivery device of FIG. 1 in a second, maximum first dose dialed, position;

Referring first to FIG. 1 there is seen a drug delivery device in accordance with the present invention. The device comprises a housing 2 within which is located a cartridge 4 containing a medicinal product, means for selecting or setting of the dose of medicinal product to be expelled and means for expelling the selected dose of medicinal product The housing 2 is generally cylindrical in shape and is divided into two compartments by a web 6 to be described in more detail below. The cartridge 4 is located within a first end of the housing 2 while the dose setting means and the means for expelling the selected dose of medicinal product are located within a second end of the housing 2.

Figure 6:
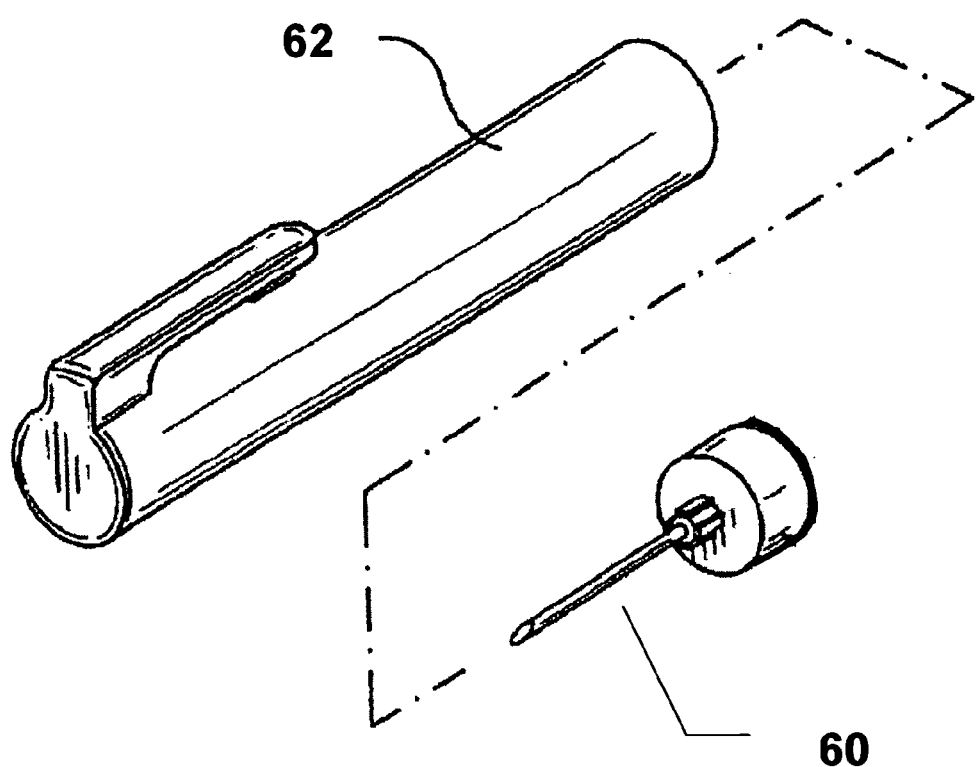
FIG. 6 shows a perspective view of a needle unit for use in a drug delivery device according to an embodiment of the invention.

The cartridge 4 may be secured in position in the first end of the housing 2 by any suitable means. In the illustrated embodiment, a cartridge retainer 12 is secured, by any suitable means, to a first side of the web to retain the cartridge in position. A needle unit such as item 60, for example, depicted in FIG. 6, may be secured to a first end of the cartridge retainer 12. The cartridge 4 further comprises a displaceable piston 10. Advancing the piston 10 towards the first end of the cartridge 4 causes the medicinal product to be expelled from the cartridge 4 through the needle unit 60. A cap 62, for example, depicted in FIG. 6 may be provided to cover the needle unit 60 when the device is not in use.

The web 6 dividing the housing 2 extends radially inwards from the cylindrical housing to define an opening 8. A piston rod 14 extends through the opening 8 in the web 6. The piston rod 14 comprises a first inner part 16 and a second outer part 18. The inner part 16 and the outer part 18 of the piston rod are keyed or ratcheted by a one-way ratchet to one another for longitudinal displacement therebetween such that rotation between the inner and outer parts of the piston rod 14 is restrained in a first direction. In the illustrated embodiment, the inner part 16 is keyed to the outer part 18 by at least one radially extending flexible barb 17 extending from the inner part 16 that runs in longitudinally extending grooves 19 on an inner surface of the outer part 18 of the piston rod 14. In the illustrated embodiment, two diametrically opposed flexible barbs 17 are used, only one of which may be seen in each view, the other being hidden.

The first inner part 16 of the piston rod 14 is provided along a second end with a threaded portion 22. The second outer part 18 of the piston rod 14 is provided along a second end with a helical rib (thread) 24 on an outer surface thereof.

A ratchet 20 is provided in the form of a number of barbs or tangs extending from the housing. The ratchet 20 prevents relative rotation between the outer part 18 of the piston rod 14 and the housing 2. The ratchet 20 also prevents the outer part 18 of the piston rod 14 from retracting counterwise back into the main housing 4, that is away from the cartridge piston 10.

The dose setting means and the means for expelling the selected dose of medicinal product will now be described in more detail.

A drive sleeve 30 is located at a second end of the piston rod 14. The drive sleeve 30 is cylindrical. A helical groove (thread) 32 extends along an internal surface of the drive sleeve 30 from a first end of the drive sleeve 30 towards an internal land 34. The land 34 is further provided with a second thread 36 for engagement with the threaded portion 22 on the inner part 16 of the piston rod 14.

The helical groove 32 and the helical rib 24 engage to permit relative rotation between the outer part 18 of the piston rod 14 and the drive sleeve 30. The second thread 36 runs in the threaded portion 22 of the inner part 16 of the piston rod 14 to permit relative rotation between the drive sleeve 30 and the inner part 16 of the piston rod 14.

The helical rib 24 and second thread 36 are opposite handed.

A dose dial sleeve 40 is of generally cylindrical form and comprises a first section of first diameter and a second section of second diameter. The first section is disposed between the drive sleeve 30 and the housing 2. An outer surface of the first section and an inner surface of the housing 2 are provided with interengaging features to provide a helical thread 41 between the housing 2 and the dose dial sleeve 40. This enables the dose dial sleeve 40 to rotate about and along the housing 2. The outer surface of the dose dial sleeve 40 is provided with numerals or other indications (not shown) of the possible doses to be dialled. The housing is provided with a window (not shown) through which a numeral or other indication representative of the users chosen dosage is displayed.

The dose dial sleeve 40 and the drive sleeve 30 are splined together. The inner surface of the dose dial sleeve 40 and the outer surface of the drive sleeve 30 are keyed together to permit only longitudinal displacement therebetween.

The second section of the dose dial sleeve 40 is of the same outer diameter as the housing 2. Within the dose dial sleeve 40 there is a shoulder 42 between the first section of the dose dial sleeve 40 and the second section of the dose dial sleeve 40. An internal surface of the shoulder 42 is provided with a plurality of radially extending longitudinally directed teeth. An internal surface of the second section of the dose dial sleeve 40 is provided with a plurality of circumferentially spaced longitudinally extending saw teeth 54. Each of the saw teeth has a radially directed surface and an inclined surface.

The second section of the dose dial sleeve 40 comprises a first recessed region in which is retained a clutch 48 and a further region in which a button 50 is retained. The button 50 is free to rotate within the second section of the dose dial sleeve 40 and is axially connected to the clutch 48. The button 50 is of generally "T" shaped configuration, the stem of which is retained within a peripheral recess provided in the clutch 48. The stem of the button 50 is provided with a peripheral bead that is retained in the peripheral recess, the button 50 being able freely to rotate with respect to the clutch and the dose dial sleeve 40, but being retained axially within the clutch 48.

The clutch includes a disc having a plurality of radially extending longitudinally directed teeth, The clutch 48 is retained on the first inner part 16 of the piston rod 14 such that there is no relative rotation therebetween. When the dose dial sleeve 40 and the clutch 48 are not forced together the respective teeth will ride over one another. Preferably, the radial separation of the respective teeth corresponds to a unit dosage. The clutch 48 is connected to the inner part 16 of the piston rod 14 such that relative rotation therebetween is prevented.

A clicker is also provided between the clutch 48 and the second section of the dose dial sleeve 40. In the illustrated embodiment, the second section of the dose dial sleeve 40 is provided with an inserted component 44 having an upper part and a lower part depending therefrom. The upper part of the inserted component 44 is provided on an internal surface with a plurality of circumferentially spaced longitudinally extending saw teeth. Each of the saw teeth has a radially directed surface and an inclined surface. The clutch 48 carries a flexible toothed member 52 about an upper region of the clutch 48 aligned with the upper part of the inserted component 44

The lower part of the inserted component 44 is in the form of a flexible toothed member normally biased in a radially outward direction. The lower part of the inserted component 44 is normally aligned with the teeth 54 provided on the internal surface of the second section of the dose dial sleeve 40.

The radial separation of the teeth on each of the dose dial sleeve 40 and the inserted component 44 preferably corresponds to a unit dosage.

Relative rotation between the dose dial sleeve 40 and the clutch 48 in a first direction will cause the flexible toothed member 52 to ride over the inclined surfaces of the saw teeth on the inserted component 44 to produce a series of clicks. Conversely, relative rotation between the dose dial sleeve 40 and the clutch 48 in a second direction opposite to the first direction will cause the flexible toothed member 52 to abut the radial surface of one of the saw teeth of the upper part of the inserted component and push the inserted component 44 in the second direction. However the lower part of the inserted component 44 is then caused to ride over the inclined surfaces of the saw teeth 54 on the dose dial sleeve 40 to produce a series of clicks.

The first direction may be selected to represent an upward or downward dialling of a dose, the second direction the converse dialling condition subject to a suitable arrangement of the flexible members and longitudinally extending teeth.

In FIG. 1, the device is provided with a prefilled cartridge 4. To operate the device a user must first select a dose. To set a dose the second section of the dose dial sleeve 40 is rotated with respect to the housing 2 outward from the housing 2. Since the drive sleeve 30 cannot rotate with respect to the dose dial sleeve 40, this is rotated out from an initial position by an amount corresponding to the desired dosage. The drive sleeve 30 is thus rotated about the helical rib 24 of the outer part 18 of the piston rod. The second thread 36 of the drive sleeve 30 thus also runs in the threaded portion 22 of the inner part 16 of the piston rod 14 drawing the inner part 16 of the piston rod 14 from the outer part 18 by a distance a function of the dosage chosen by a user. When a dose is dialled, the drive sleeve 30 descends on an inner part 16 of the piston rod a distance equal to the distance required to displace the cartridge piston 10 to expel the selected dose of medical product.

In the illustrated embodiment, on dialling up of a dose the relative rotation between the dose dial sleeve 40 and the clutch 48 (fixed rotationally with respect to the inner part 16 of the piston rod 14) causes the flexible toothed member of the inserted component 44 to ride over the teeth 54 on the dose dial sleeve 40 to create a series of clicks. This is an audible confirmation of the dose being dialled. On dialling down, the inserted component 44 is locked to the dose dial, and the flexible member 52 acts on the teeth of inserted component 44. In this way an audible confirmation of the dialling action of a user is produced.

The user may rotate the dose dial sleeve 40 to increase or decrease the amount of the dosage selected to be delivered. Conveniently, the first section of the dose dial sleeve 40 is provided with a marked scale, which together with associated features of the housing, enable a user to determine the amount of the dosage selected to be delivered. The associated features of the housing 2 may include a window formed in the housing 2 or a marking on the housing 2 for alignment with the marked scale.

Once a desired dose has been set (as shown in FIG. 2), to deliver the dose the user depresses the button 50 to urge the button 50 and associated clutch 48 towards the first end of the housing 2. When the button 50 is depressed the clutch 48 is driven into the second section of the dose dial sleeve 40 to prevent relative rotation between the dose dial sleeve 40 and the inner part 16 of the piston rod 14. The button 50 may still rotate with respect to the dose dial sleeve and the drive sleeve 30. Further longitudinal movement of the button 50 causes the dose dial sleeve 40 (together with the drive sleeve 30) to rotate towards the first end of the device. As the dose dial sleeve 40 travels into the housing 2, rotation of the drive sleeve 30 (keyed to the dose dial sleeve 40) forces the outer part 18 of the piston rod 14 to move axially with respect to the housing 2.

Rotation of the inner part 16 of the piston rod 14 within the outer part 18 of the piston rod 14 as the button is advanced towards the first end of the housing 2 causes the barb 17 to run across the grooves 19 to provide tactile and audible feedback as each unit of medicinal product is dispensed. It may be seen that preferably, the angular spacing of the grooves 19 preferably corresponds to a unit dose.

Figure 3:
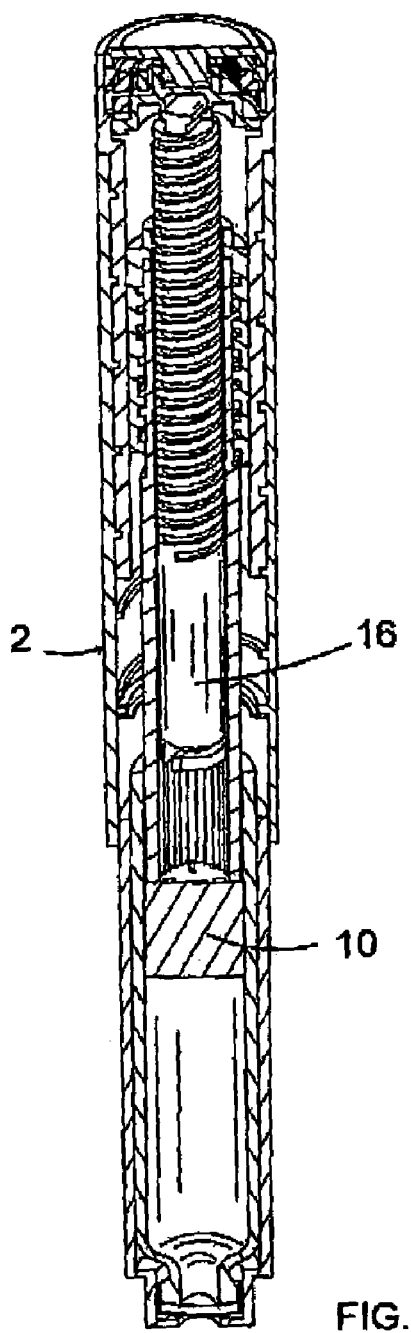
FIG. 3 shows a sectional view of the drug delivery device of FIG. 1 in a third, maximum first dose dispensed, position.

The outer part 18 of the piston rod 14 continues to advance until the dose dial sleeve 40 has returned to the initial position in relation to the housing and the drive sleeve has returned to its initial position in relation to the outer part 18 of the piston rod 14 (FIG. 3).

Figure 4:
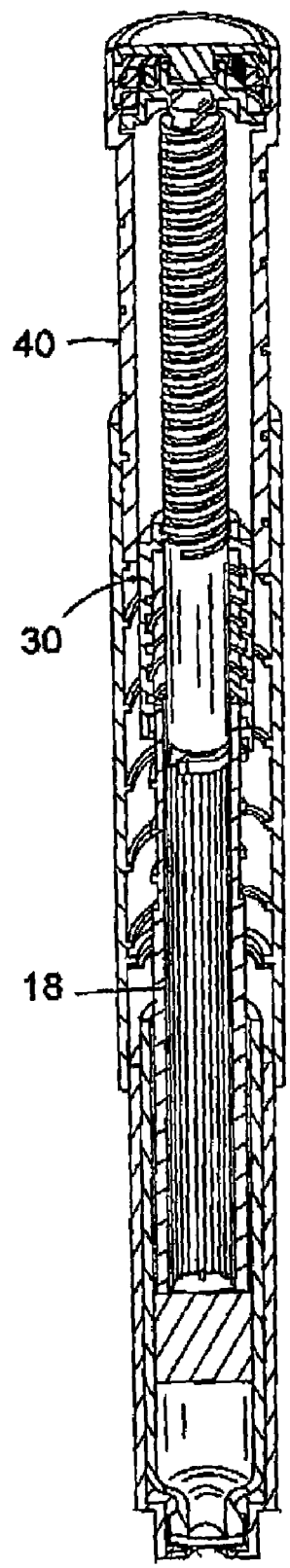
FIG. 4 shows a sectional view of the drug delivery device of FIG. 1 in a fourth, final dose dialed, position.

Further dosages may be delivered as required. FIG. 4 shows an example of a subsequently selected dosage. It will be noted that the drive sleeve 30 has advanced further along the threaded portion 22 of the inner part 16 of the piston rod 14. The position of the drive sleeve 30 along the threaded portion 22 corresponds to the amount of medicinal product remaining in the cartridge 4, such that when the drive sleeve 30 reaches the end of the threaded portion 22 and can rotate no further, this corresponds to no medicinal product remaining in the cartridge 4. It will be seen that if a user seeks to select a quantity of medical product greater than that remaining in the cartridge 4, this cannot be done since when the drive sleeve 30 stops rotating this prevents further rotation of the dose dial sleeve 40 and setting of a larger dose.

Figure 5:
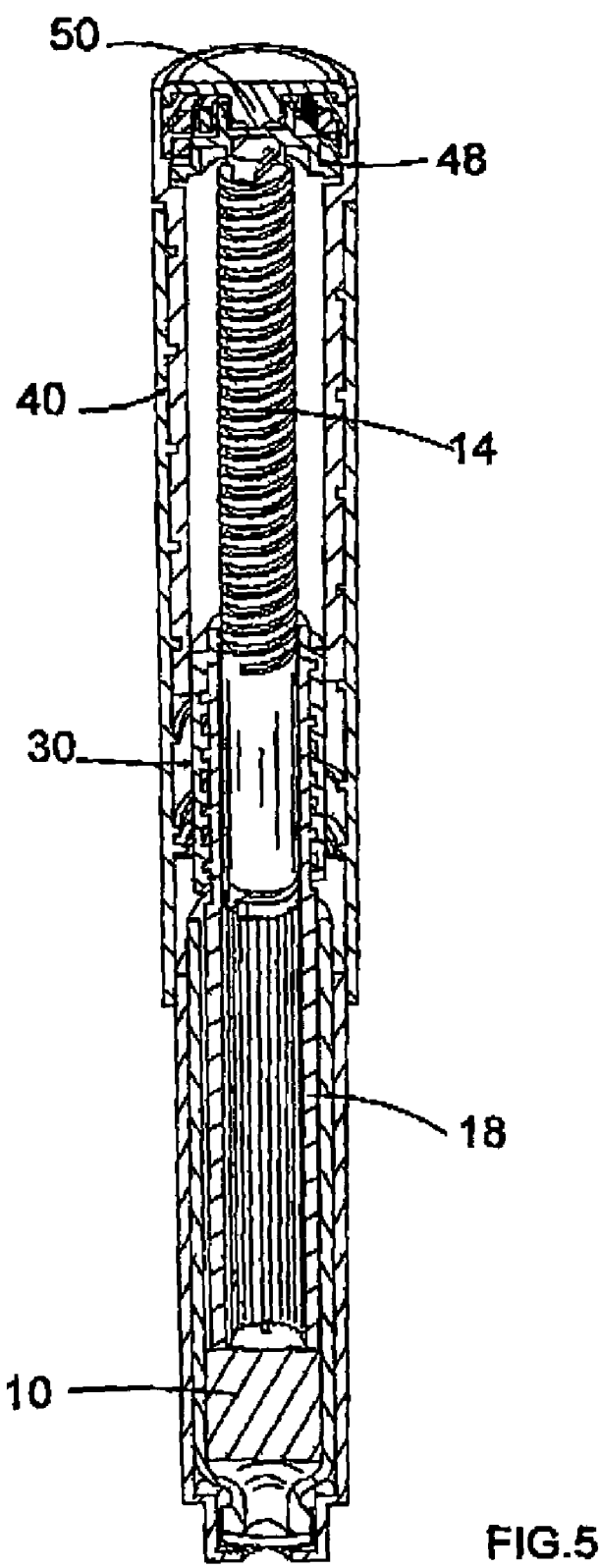
FIG. 5 shows a sectional view of the drug delivery device of FIG. 1 in a fifth, final dose dispensed, position.

FIG. 5 shows a device according to the present invention in which the entire medical product within the cartridge 4 has been expelled.

The invention claimed is:

1. A drive mechanism for use in a drug delivery device comprising:
   a housing;
   a dose dial sleeve having a helical thread of a first lead; and
   a two-part piston rod; characterised in that the two-part piston rod comprises an outer part having a helical thread of a second lead and an inner part having a helical thread of a third lead, whereby the first lead of the thread of the dose dial sleeve is equal to the sum of the second lead of the thread of the outer part of the piston rod and the third lead of the thread of the inner part of the piston rod.

2. The method of manufacturing or assembling a drug delivery device, comprising the step of providing a drive mechanism according to claim 1.

3. An assembly for use in a drug delivery device comprising a drive mechanism including:
   a housing;
   a dose dial sleeve having a helical thread of a first lead; and
   a two-part piston rod; characterised in that the two-part piston rod comprises an outer part having a helical thread of a second lead and an inner part having a helical thread of a third lead, whereby the first lead of the thread of the dose dial sleeve is equal to the sum of the second lead of the thread of the outer part of the piston rod and the third lead of the thread of the inner part of the piston rod.

4. A method of manufacturing or assembling a drug delivery device, comprising providing the assembly of claim 3.

5. A drug delivery device comprising a drive mechanism comprising:
   a housing;
   a dose dial sleeve having a helical thread of a first lead; and
   a two-part piston rod; characterised in that the two-part piston rod comprises an outer part having a helical thread of a second lead and an inner part having a helical thread of a third lead, whereby the first lead of the thread of the dose dial sleeve is equal to the sum of the second lead of the thread of the outer part of the piston rod and the third lead of the thread of the inner part of the piston rod.

6. The drug delivery device according to claim 5, wherein the delivery device is a pen-type device.

7. The drug delivery device according to claim 5, wherein the delivery device is an injector-type device.

8. The drug delivery device according to claim 5, wherein the device further comprises a needle.

9. The drug delivery device according to claim 5, wherein the device is a needle-free device.

10. A method of delivering a drug, comprising:
    providing the device of claim 5, and
    dispensing a medicinal product with the device.

11. The method of claim 10, wherein dispensing a medicinal product includes dispensing a pharmaceutical formulation comprising an active compound selected from the group consisting of insulin, growth hormone, low molecular weight heparin, analogues thereof, and derivatives thereof.

12. A drug delivery device comprising an assembly, the assembly including a drive mechanism including:
    a housing;
    a dose dial sleeve having a helical thread of a first lead; and
    a two-part piston rod; characterised in that the two-part piston rod comprises an outer part having a helical thread of a second lead and an inner part having a helical thread of a third lead, whereby the first lead of the thread of the dose dial sleeve is equal to the sum of the second lead of the thread of the outer part of the piston rod and the third lead of the thread of the inner part of the piston rod.

13. The drug delivery device of claim 12, wherein the device is a pen-type device.

14. The drug delivery device of claim 12, wherein the device is an injector-type device.

15. The drug delivery device of claim 12, further comprising a needle.

16. The drug delivery device of claim 12, wherein the device is a needle-free device.

17. A method of delivering a drug, comprising:
    providing the device of claim 12, and
    dispensing a medicinal product with the device.

18. The method of claim 17, wherein dispensing a medicinal product includes dispensing a pharmaceutical formulation from the device, wherein the pharmaceutical formulation comprises an active compound selected from the group consisting of insulin, growth hormone, low molecular weight heparin, analogues thereof, and derivatives thereof.

* * * * *